(12) United States Patent
Campbell et al.

(10) Patent No.: US 8,282,211 B2
(45) Date of Patent: Oct. 9, 2012

(54) METHOD AND APPARATUS FOR IMPROVED FUNDUS IMAGING THROUGH CHOICE OF LIGHT POLARISATION

(76) Inventors: Melanie C. W. Campbell, Waterloo (CA); Juan Manuel Bueno Garcia, Marcia (ES)

( * ) Notice: Subject to any disclaimer, the term of this patent is extended or adjusted under 35 U.S.C. 154(b) by 409 days.

(21) Appl. No.: 12/226,970

(22) PCT Filed: May 3, 2007

(86) PCT No.: PCT/CA2007/000750
§ 371 (c)(1),
(2), (4) Date: Jan. 22, 2009

(87) PCT Pub. No.: WO2007/124601
PCT Pub. Date: Nov. 8, 2007

(65) Prior Publication Data
US 2009/0310083 A1 Dec. 17, 2009

Related U.S. Application Data

(60) Provisional application No. 60/796,899, filed on May 3, 2006.

(51) Int. Cl.
*A61B 3/10* (2006.01)
(52) U.S. Cl. .................. 351/215; 351/246; 351/205
(58) Field of Classification Search .............. 351/205, 351/215, 246
See application file for complete search history.

(56) References Cited

U.S. PATENT DOCUMENTS

| 578,789 | A | | 8/1998 | Reiter et al. | |
|---|---|---|---|---|---|
| 5,787,890 | A | * | 8/1998 | Reiter et al. | 600/476 |
| 588,081 | A | | 3/1999 | Thall | |
| 602,721 | A | | 2/2000 | Guyton et al. | |
| 6,112,114 | A | | 8/2000 | Dreher | |
| 6,540,357 | B1 | * | 4/2003 | Ohnuma et al. | 351/215 |
| 2002/0091323 | A1 | * | 7/2002 | Dreher | 600/476 |
| 2004/0012853 | A1 | | 1/2004 | Garcia et al. | |

FOREIGN PATENT DOCUMENTS

GB 440735 1/1936
JP 200604517 A2 8/2006
* cited by examiner

*Primary Examiner* — James Greece

(57) ABSTRACT

The present invention provides a method and device to image the fundus of the eye using polarized light which includes circular polarization. The invention is most broadly comprised of a device to generate polarization states of light, including circularly polarized light (i.e. potentially combinations of elliptically polarized light and depolarized light combined, elliptically polarized light alone, or circularly polarized light with depolarized light or circularly polarized light alone). This light can be used with any fundus imaging device including but not limited to fundus cameras, scanning laser ophthalmoscopes, confocal scanning laser ophthalmoscopes, optical coherence tomography instruments, with or without some form of wavefront correction. This is a change from common fundus imaging systems which use randomly polarized light or linearly polarized light. The simplest implementation of this is a quarter wave plate (or equivalent retarder) combined with a linear polarizer located after the light source and before the eye. The QWP can be rotated to produce differing circular and elliptical polarizations of light which are ideal for imaging differing structures at the rear of the eye for different people.

17 Claims, 9 Drawing Sheets $$(S'_0 \quad S'_1 \quad S'_2 \quad S'_3) = \begin{pmatrix} m_0 & m_0 & m_0 & m_0 \\ m_{10} & m_{11} & m_1 & m_{13} \\ m_2 & m_2 & m_2 & m_2 \\ m_{30} & m_{31} & m_3 & m_{33} \end{pmatrix} \cdot (S_0 \quad S_1 \quad S_2 \quad S_3)$$

Figure 2

METHOD AND APPARATUS FOR IMPROVED FUNDUS IMAGING THROUGH CHOICE OF LIGHT POLARISATION

CROSS REFERENCE TO RELATED U.S. APPLICATIONS

This patent application is a National Phase application claiming the benefit of PCT/CA2007/000750 filed on May 3, 2007; which further claims the priority benefit from, U.S. Provisional Patent Application Ser. No. 60/796,899 filed on May 3, 2006, in English, entitled METHOD AND APPARATUS FOR IMPROVED FUNDUS IMAGING THROUGH CHOICE OF LIGHT POLARISATION, and which is incorporated herein by reference in its entirety.

FIELD OF THE INVENTION

The present invention relates to a device to image the fundus of the eye using polarized light which includes circular polarization. The use of circularly polarized light also means that the polarization vector orientation of the input light rotates continuously in space and time which is important to image quality. More particularly the present invention relates to a device to generate polarization states of light, including elliptically polarized light alone, circularly polarized light alone, a combination of elliptically polarized light and depolarized light, and a combination of circularly polarized light and depolarised light

BACKGROUND OF THE INVENTION

Light coming from structures in fundus images is differentially polarised, leading to clinical applications such as assessment of glaucoma and foveal fixation. Using polarisation, it has been shown to be possible to obtain objective image improvement in visualisation of the retinal structures, see references 1-4 listed after the description. Nevertheless, improvements are needed to obtain better images of the fundus for visualization, diagnosis and guided therapy.

Therefore it would be very advantageous to provide a method and apparatus to provide better imaging of the fundus of the eye to improve the diagnosis of abnormalities of the optic nerve head (ONH), and of other structures which interact with polarized light, including but not limited to those that change in glaucoma. This methodology may also improve visualization of other structures at the rear of the eye, for example blood vessels important to the diagnosis of diabetic retinopathy and age related macular degeneration among others. In addition bacteria and parasites and other invading cells and organisms may also be better visualized.

SUMMARY OF THE INVENTION

Embodiments of methods and devices to image the fundus of the eye using polarized light which includes circular polarization are provided. In its broadest, the present invention provides a device to generate polarization states of light, including circularly polarized light alone, elliptically polarized light alone, combinations of elliptically polarized light and depolarized light combined, or circularly polarized light with depolarised light. This light can be used with any fundus imaging device including but not limited to fundus cameras, scanning laser ophthalmoscopes, confocal scanning laser ophthalmoscopes, optical coherence tomography instruments, with or without some form of wavefront correction. This is an improvement from common fundus imaging systems which use randomly polarized light or one linear polarization state of light or multiple linear polarization states of light.

Thus, in one aspect of the present invention, there is provided an apparatus for imaging the fundus of the eye using non-linearly polarized light, comprising:

a light source for generating a beam of light;

an optical element configured to generate a desired non-linear polarization state of light in said beam of light passing therethrough, wherein said desired non-linear polarization state of light includes any one of circularly polarized light alone and elliptically polarized light alone and excludes linearly polarized light alone;

first light directing and focusing optics configured for directing the beam of light having said desired polarization state onto a fundus of a subject's eye; and second light directing and focusing optics configured for directing the beam of light reflected from the fundus of a subject's eye into an imaging detector configured for receiving images of the fundus of the eye after illumination by the beam of light, said second light directing and focusing optics being configured for collecting and imaging the beam of light coming from the pupil of the eye with minimal effect on its polarization state.

In this aspect of the invention the optical element may be a quarter wave plate (or equivalent retarder) combined with a linear polarizer located after the light source and before the eye.

In another aspect of the present invention, there is provided a method for imaging the fundus of the eye using a beam of non-linearly polarized light, comprising:

a) generating a beam of non-linearly polarized light having a desired polarization state, the desired polarization state including any one of circularly polarized light alone and elliptically polarized light alone and excluding linearly polarized light alone;

b) directing and focusing the beam of said non-linearly polarized light onto the fundus of the eye using first light directing and focusing optics; and c) directing and focusing a reflected beam of light containing information of the fundus of the eye onto a detector using second light directing and focusing optics, said second light directing and focusing optics being configured for collecting and imaging the beam of light coming from a pupil of the eye with a minimal effect on its polarization state, and producing an image of the fundus of the eye.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which:

FIG. 2 shows the input and measured polarised light represented by the Stokes Vectors S and S', respectively, where the top row of the Mueller matrix, $M_{0j}$, represents the modulation effect of the tissue on the incoming light;

DETAILED DESCRIPTION OF THE INVENTION

Generally speaking, the systems described herein are directed to devices to image the fundus of the eye using polarized light. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to devices to image the fundus of the eye using polarized light, with more general properties than currently used.

Light coming from structures in fundus images is differentially polarised, leading to clinical applications such as assessment of glaucoma and foveal fixation. Using polarisation, it has been shown to be possible to obtain objective image improvement in visualisation of the retinal structures, see references 1-4.

The purpose of the study from which the present invention is based was to explore the subjective quality of fundus images obtained directly through polarimetry and reconstructed using Mueller matrix polarimetry (as disclosed in U.S. Pat. No. 6,927,888, issued Aug. 9, 2005, entitled "Method And Apparatus For Imaging Using Polarimetry And Matrix Based Image Reconstruction", which is incorporated herein by reference in its entirety) in combination with various image quality metrics.

Figure 1:
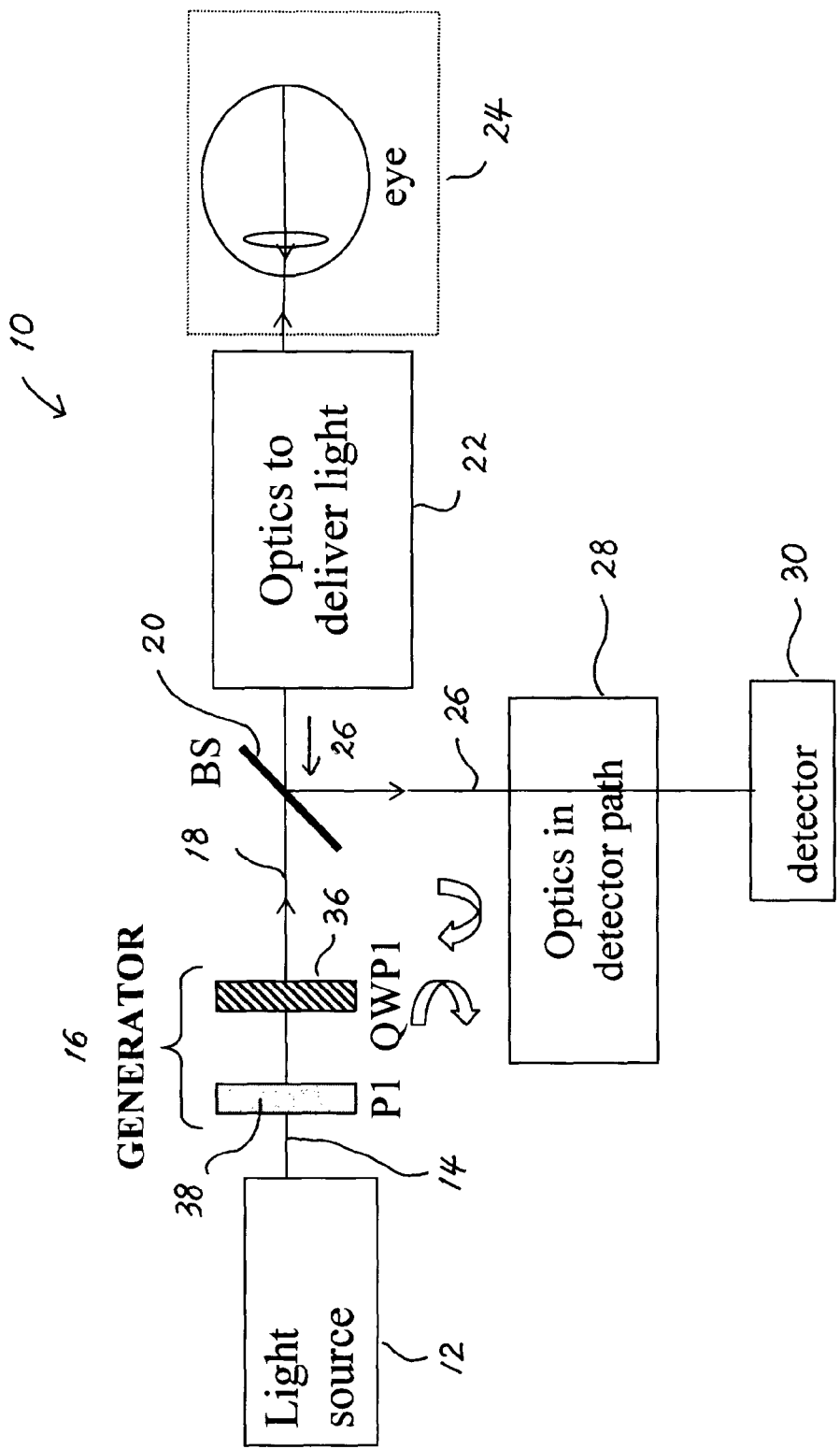
FIG. 1 shows a polarization generator comprised of a linear polarizer (P1) and a quarter wave plate (QWP) positioned in the input path.

The present invention provides a method and device to image the fundus of the eye using polarized light which includes circular polarization. Referring to FIG. 1, an apparatus shown generally at 10 includes a light source 12 which produces a beam of light (coherent or incoherent, of a visible or infrared wavelength, and of any polarization) 14 and optic element 16 to generate polarization states of light, including elliptically polarized light alone, combinations of elliptically polarized light and depolarized light combined, elliptically polarized light alone, circularly polarized light in combination with depolarized light, or circularly polarized light alone when the beam 14 passes through the optics 16. The light beam 18 having the desired polarization properties produced by the light beam 14 passing through the optical element 16 is passed through a beam splitter 20 or other device separating the ingoing and outgoing paths of light after which it passes through optics 22 which directs the beam to a patient's eye 24. The light beam reflected by the fundus returns through optics 22 and into the eye after which this reflected beam 26 carrying the image of the fundus is split and the beam 26 is directed to a detector 30 after passing through optics 28.

The optical element 16 is configured to generate any one of circularly polarized light alone, elliptically polarized light alone, a combination of elliptically polarized light and depolarized light, and a combination of circularly polarized light with depolarised light.

The optical element 16, in its simplest implementation, may be comprised of a quarter wave plate (QWP) 36 (or equivalent retarder) combined with a linear polarizer 38, with the polarizer 38 and quarter wave plate 36 located after the light source 12 and before the eye 24, with the polarizer 38 located between the quarter wave plate 36 and the light source 12. The QWP 36 can be rotated to produce differing circular and elliptical polarizations of light which are ideal for imaging differing structures at the rear of the eye for different people. The light source 12 may be configured to produce linearly polarized light in which case the linear polarizer 38 is not required, and once again the QWP 36 can be rotated to produce differing circular and elliptical polarizations of light.

Other embodiments may include any other retarder which causes two perpendicular linear polarizations to be either 90 or 180 degrees out of phase producing circularly polarized light or causes them to be out of phase by an amount different than 0, 90 or 180 degrees, producing elliptically polarized light.

Another specific example of a retarder is a birefringent liquid crystal device of sufficient thickness and orientation to the linear polarizer to cause two perpendicular polarization states of light to be 90 or 180 degrees out of phase. If the light source 12 produces linearly polarized light, then optical element 16 need only be comprised of an optical retarder oriented properly with respect to the linear polarization. Embodiments giving elliptically polarized light are those that cause the two linear polarizations to be out of phase by amounts different from 0, 90 or 180 degrees (produced in one implementation by rotating a QWP with respect to the axis of linear polarization of entering light in any orientation other than those which produce circular or linear polarizations).

Another embodiment useful for producing elliptically polarized light is to produce two perpendicular polarizations of light with differing relative intensities incident on a retarder which causes the two polarizations to be out of phase by an amount different from 0 degrees (including retardations of 90 or 180 degrees).

Another embodiment is to combine circularly polarized light with linear polarized light oriented in any direction to produce any type of elliptically polarized light. In order to produce elliptically or circularly polarized light in combination with depolarized light, a depolarizing element should be introduced after optical element 16, or optical element 16 should depolarize a portion of the light incident on it.

The optics 22 used to deliver light beam 18 to the eye 24 may include the input path of any fundus imaging device including but not limited to fundus cameras, scanning laser ophthalmoscopes, confocal scanning laser ophthalmoscopes, optical coherence tomography instruments, with or without some form of wavefront correction. The key is that the light with the desired polarization states is directed into the entrance pupil of the eye by any combination of lenses or mirrors or apertures or other optomechanical components without loss of circular polarization and that the light is focused onto the fundus with a fixed or variable position of focus.

The optics 28 used to deliver the reflected light beam 26 to the detector 30 may include the output arm of any fundus imaging device including but not limited to fundus cameras, scanning laser ophthalmoscopes, confocal scanning laser ophthalmoscopes, optical coherence tomography instruments, with or without some form of wavefront correction which collects and images the light coming from the pupil of the eye with minimal impact on its polarization state. This arm will use lens(es), mirror(s) or other optomechanical devices to focus the fundus plane of interest onto the detector 30. Some of the optics 22 and 28 may be common.

The apparatus for producing circular, elliptical or both mixed with depolarized light disclosed herein may be retrofitted into existing devices for imaging the eye. It may be placed in the input arm following the light source including but not limited to fundus cameras, scanning laser ophthalmoscopes, confocal scanning laser ophthalmoscopes, optical coherence tomography instruments, with or without some form of wavefront correction. This is a change from common fundus imaging systems which use randomly polarized light or linearly polarized light. A similar device called an analyzer which can sample varying polarization states of light returning to the detector may be placed in the reflected beam path of any existing fundus imaging device including but not limited to fundus cameras, scanning laser ophthalmoscopes, confocal scanning laser ophthalmoscopes, optical coherence tomography instruments, with or without some form of wavefront correction.

An initial demonstration was with a confocal scanning laser ophthalmoscope (Example below) where images of the optic nerve head area were preferred by a clinician (with no knowledge of the polarizations) if they were formed with input light containing circular polarization, usually elliptically polarized light. This image could be formed directly by inputting the light of the polarization state which forms the preferred image.

Alternately the inventors have previously shown in U.S. Pat. No. 6,927,888, issued Aug. 9, 2005, entitled "Method And Apparatus For Imaging Using Polarimetry And Matrix Based Image Reconstruction", which is incorporated herein by reference in its entirety that the image can be reconstructed from images corresponding to four different input polarizations.

When four different polarizations are used, images can be reconstructed which correspond to polarization states for each position on the Poincaré sphere. Thus images corresponding to a range of circularly, linearly and elliptically polarized light can be reconstructed. A clinician's preference for images reconstructed corresponding to polarization states which contained circularly polarized light was clear. Preferred images are marked in FIGS. 3 and 4 by coded bars corresponding to the feature being observed. Such polarizations can improve the visibility and clarity of clinically important features and potentially improve the resolution of such features.

Images presented for a clinician to evaluate included those corresponding to specific polarization states of light and also those in which specific image quality metrics were maximized or minimized, using a methodology previously patented by the inventors in U.S. Pat. No. 6,927,888. This patent specified the use of any image quality metric but gave specific examples of the Signal to noise (SNR) metric. In this work, the images preferred by a clinician for the optic nerve head features were images included those taken with circular and elliptical polarizations states of input light and images which corresponded to a minimization of the image quality metric, entropy, a minimization of the image quality metric acutance and a maximization of the image quality metric, entropy. This was reproducible across subjects and on two different evaluation dates. When a clinician evaluated images of blood vessels, again images formed by incident elliptical and circular polarizations were preferred. The image quality metrics of minimum acutance, maximum entropy, maximum acutance and maximum SNR were preferred. In some cases the images were directly measured and again in some cases they were formed when the reconstruction assumed that circular or elliptically polarized incident light was incident on the rear of the eye (see FIG. 6).

This novel method is expected to improve the diagnosis of abnormalities of the optic nerve head and the retinal nerve fiber layer, including but not limited to, glaucoma. This methodology may also improve visualization of other structures at the rear of the eye, for example blood vessels important to the diagnosis of diabetic retinopathy and age related macular degeneration among others. In addition bacteria and parasites and other invading cells and organisms may also be better visualized.

Figure 7:
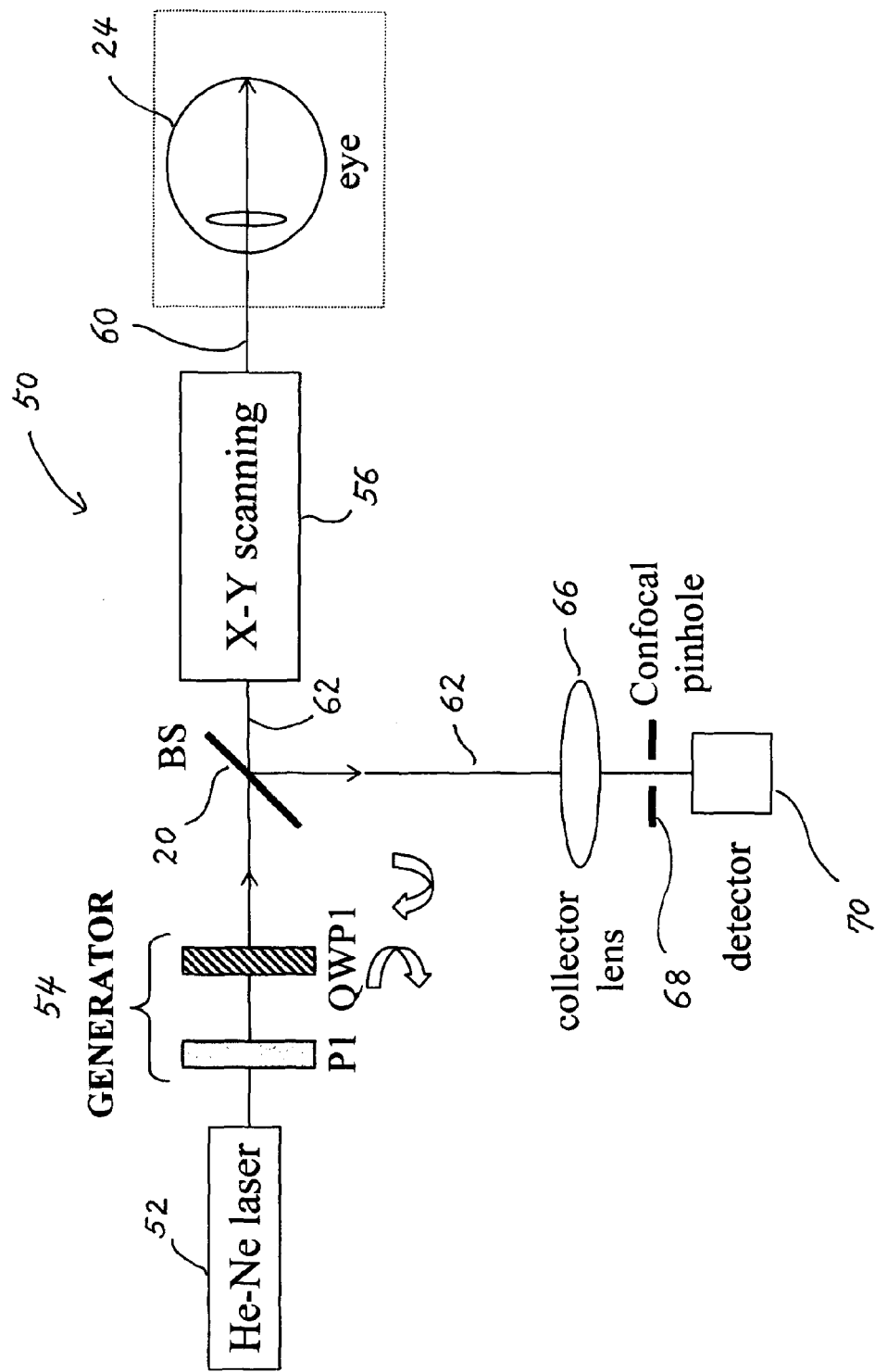
FIG. 7 shows a confocal scanning laser ophthalmoscope with a generator constructed in accordance with the present invention which is capable of providing the required polarization states of light.

FIG. 7 shows a confocal scanning laser ophthalmoscope at 50 which uses a laser beam of visible or infrared wavelength (He—Ne for this experiment) 52 with a generator 54 capable of providing the required polarization states of light. Beamsplitter 20 operates the same as in apparatus 10 in FIG. 1. An X-Y scanning stage 56 provides for displacement of the light beam 60 with respect to the fundus at the rear of the patient's eye. The reflected light beam 62 carrying the image information about the back of the eye passes through a collector lens 66 which focuses the beam through the confocal pinhole 68 and onto detector 70.

The invention will be illustrated using the following non-limiting example.

EXAMPLE

Polarisation images were obtained using the confocal scanning laser ophthalmoscope (CSLO) shown in FIG. 7. Four video segments of the ONH (10° and 15° fields) were recorded for differing generator polarisation states.

At each polarisation state, eight frames were registered, averaged and used to calculate the top row of the Mueller matrix for each pixel, see FIG. 2. Images evaluated corresponded to recorded images for input states of linear polarisation (00), circular polarisation (45) and elliptical polarisation (30, 60), as well as the calculated unpolarized light (M00) image. Images were reconstructed by incrementing the incident Stokes vector in degree steps on the Poincaré sphere and some of these images producing maximum or minimum values of an image quality metric were also evaluated.

When circularly polarized light is used as the input, the image produced by the reflected light is often of better quality than images produced with linearly polarized light. On other occasions, when elliptically polarized light is used as the input, the image produced by the reflected light is often of better quality than images produced with linearly polarized light.

When the step of reconstructing images from the initial four images taken (fully described in the previous patent) is included, we can predict the polarization state of incident light that would produce an image with the highest quality, defined by a metric. The polarization states for which quality can be predicted are all circular, linear and elliptical polarizations. This incident light producing the maximum or minimum metric value in general has elliptical polarization, indicating that elliptically polarized light (or light that contains circular polarization) produces higher quality images than linearly polarized incident light.

Those images evaluated in our example had minimum and maximum values of the image quality metrics: signal-to-noise ratio (SNR), entropy (ENT) and acutance (ACU). Image recordings were repeated on subsequent days (Subject 1 and 2) (FIGS. 3 and 4) and at ±0.50D of defocus (Subject 1) (FIG. 5). A clinician, masked to the process of image generation, subjectively evaluated the entire set of images and ranked them. Clinically relevant features of the optic nerve head were evaluated: optic cup (shape and size); lamina cribrosa visibility; neuroretinal rim (NRR) visibility; the retinal nerve fibre layer (RNFL) and the ONH vasculature.

The following rating scale was used:
1: Not Visible, 2: Poor Visibility, 3: Satisfactory Visibility, 4: Good Visibility The evaluations were repeated several months later on the same image sets. Overall, the data indicates that images containing more complex polarization information were preferred for evaluation of the optic nerve head and retinal structures to images of M00 and linear polarization (00) alone.

1) Optic Nerve Cup & Lamina Cribrosa:
Circular and elliptical polarization orientations were preferred for visualization of the cup. The preferred polarization state was different at different focus depths but preferred states, coded by hatched bars include circular and elliptical polarizations (FIG. 4).

2) Neural Retinal Rim Edge and Vessels:
Across the two individuals, images of M00 and Min ACU (vessels, corresponding to elliptically polarized light), and MOO and circularly polarized light (NRR Edge) were most highly ranked.

3) Retinal Nerve Fibre Layer:
Max ACU and Min ENT constructed images (with elliptically polarized light) were preferred for images taken nearer to the plane of the retinal nerve fiber layer.

M00, Min ACU and Max SNR (constructed with elliptically polarized light) were consistent across subjects for visualization of the blood vessels. Other measurements by the inventors have shown that vessels contrast is improved in images of the near periphery for constructed images which maximize entropy using elliptically polarized light.

Figure 3:
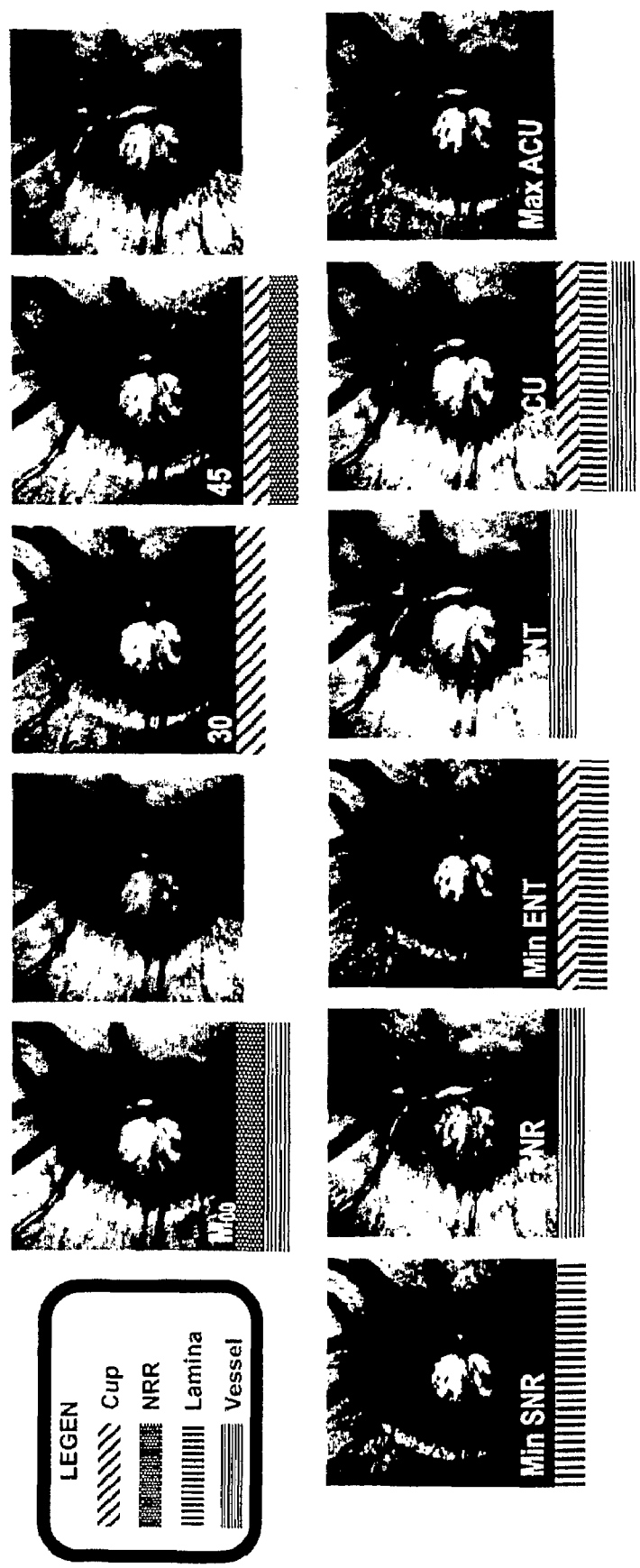
FIG. 3 shows optic nerve head structures of subject 1 obtained using the method and apparatus disclosed herein.
Figure 4:
FIG. 4 shows optic nerve head structures of subject 2 obtained using the method and apparatus disclosed herein (top row) and derived by calculation from the images using the method disclosed in U.S. Pat. No. 6,927,888, issued Aug. 9, 2005, entitled "Method And Apparatus For Imaging Using Polarimetry And Matrix Based Image Reconstruction", which is incorporated herein by reference in its entirety, (bottom row)
Figure 5:
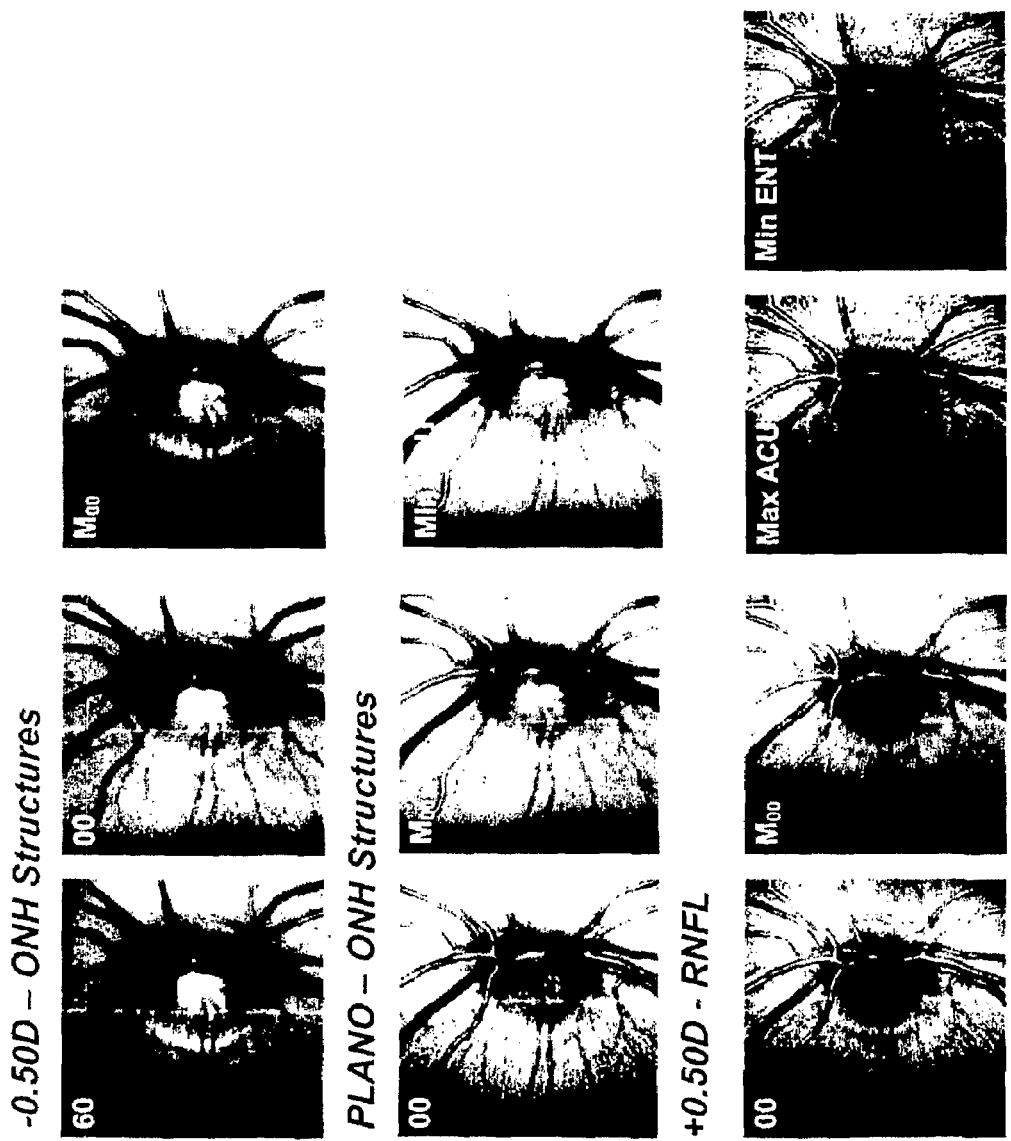
FIG. 5 shows the effect of focusing plane for upper row for this subject a −0.50D lens was used with the apparatus and ONH structures near the base of the ONH are imaged, for middle row for this subject a plano lens was used with the apparatus to image ONH structures anterior to the structures in the upper row, and for lower row for this subject a +0.50D lens was used to image structures anterior to the middle row and close to the Retinal Nerve Fiber Layer.

FIG. 3 shows optic nerve head structures of subject 1 obtained using the method and apparatus disclosed herein and FIG. 4 shows optic nerve head structures of subject 2. These Figures show an example, for each subject, of a complete set of the evaluated images. The line beneath the image indicates that it was selected as 'Satisfactory' or 'Good' on repeated evaluations for a particular feature. Subject 2 had little cupping so evaluations were not made for the cup or lamina cribrosa. The polarization state of the measured images are given in the lower left corners of the images in the top row. The minimum or maximum metric that gave the reconstructed images is given in the lower left corner of images in the second row. Max SNR (indicated by an asterisk) was not ranked highest across all evaluations but was ranked highly across subjects for viewing the vessels.

FIG. 5 shows the effect of focusing plane, where, for the upper row for this subject, a −0.50D lens used with the apparatus which focused ONH structures near the base of the ONH, for the middle row for this subject a plano lens was used with the apparatus to image ONH structures anterior to the structures in the upper row, and for the lower row for this subject a +0.50D lens was used to image structures anterior to the middle row and close to the retinal nerve fiber layer. The polarization state of the measured image or the minimum or maximum metric that gave the constructed images that were selected in repeated evaluations for viewing features at the optic nerve head are shown in the upper left of the images. Towards the base of the cup (−0.50D) raw polarization inputs of 60 (elliptical) and 00 were preferred. With no defocus in place, Min ACU was preferred for visualization of the internal ONH structures. At the anterior position of focus (+0.50D), Max ACU and Min ENT were preferred for visualization of the RNFL. Reference images (M00 and 00) are also given for comparison.

Figure 6A:
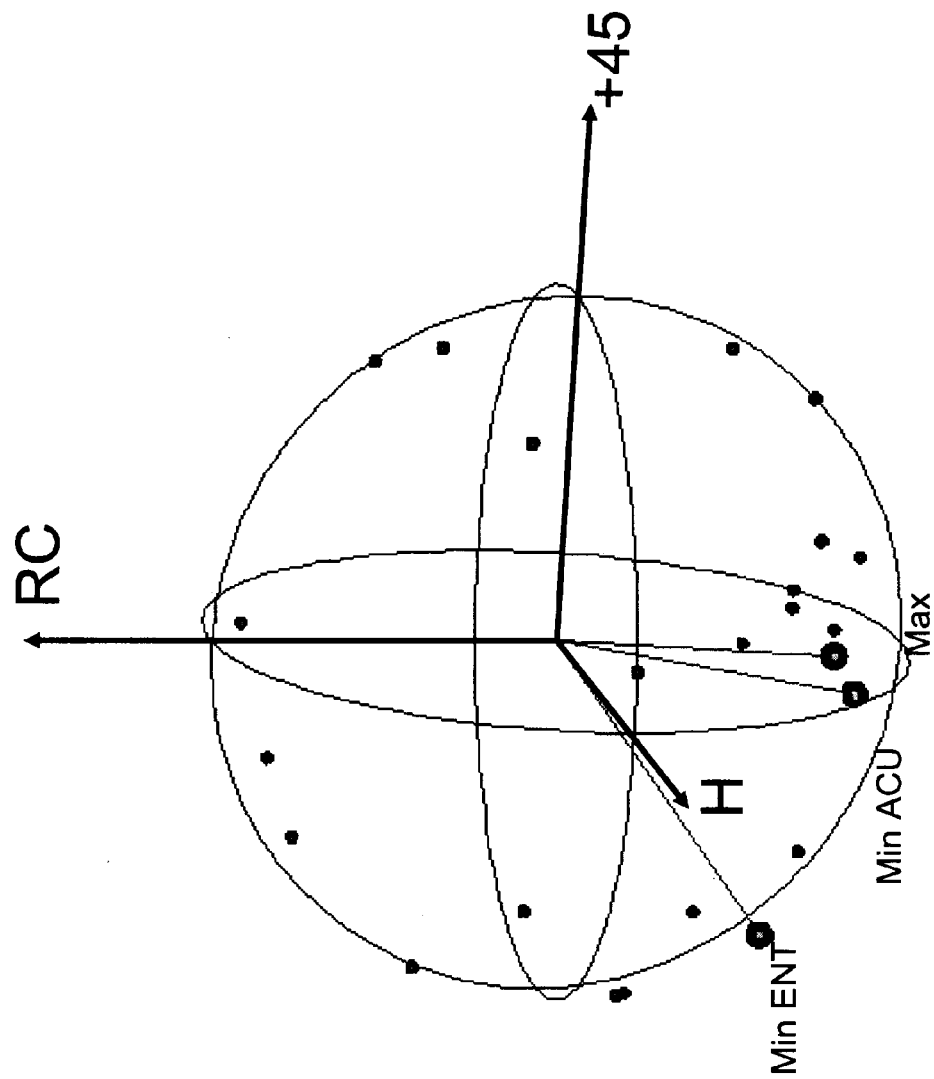
FIGS. 6a, 6b and 6c show Poincaré spheres for images with maximum and minimum values of metrics of ONH features.
Figure 6B:
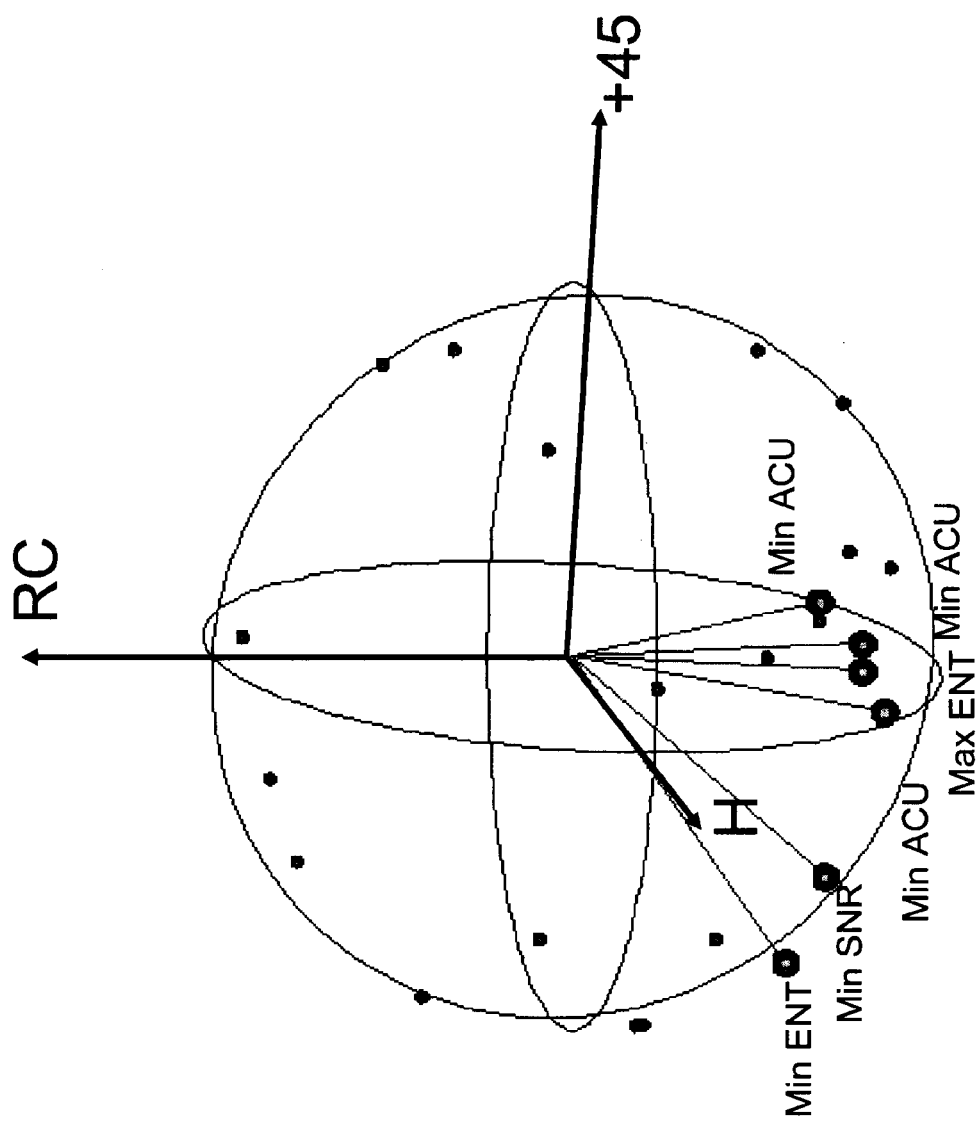
Figure 6C:
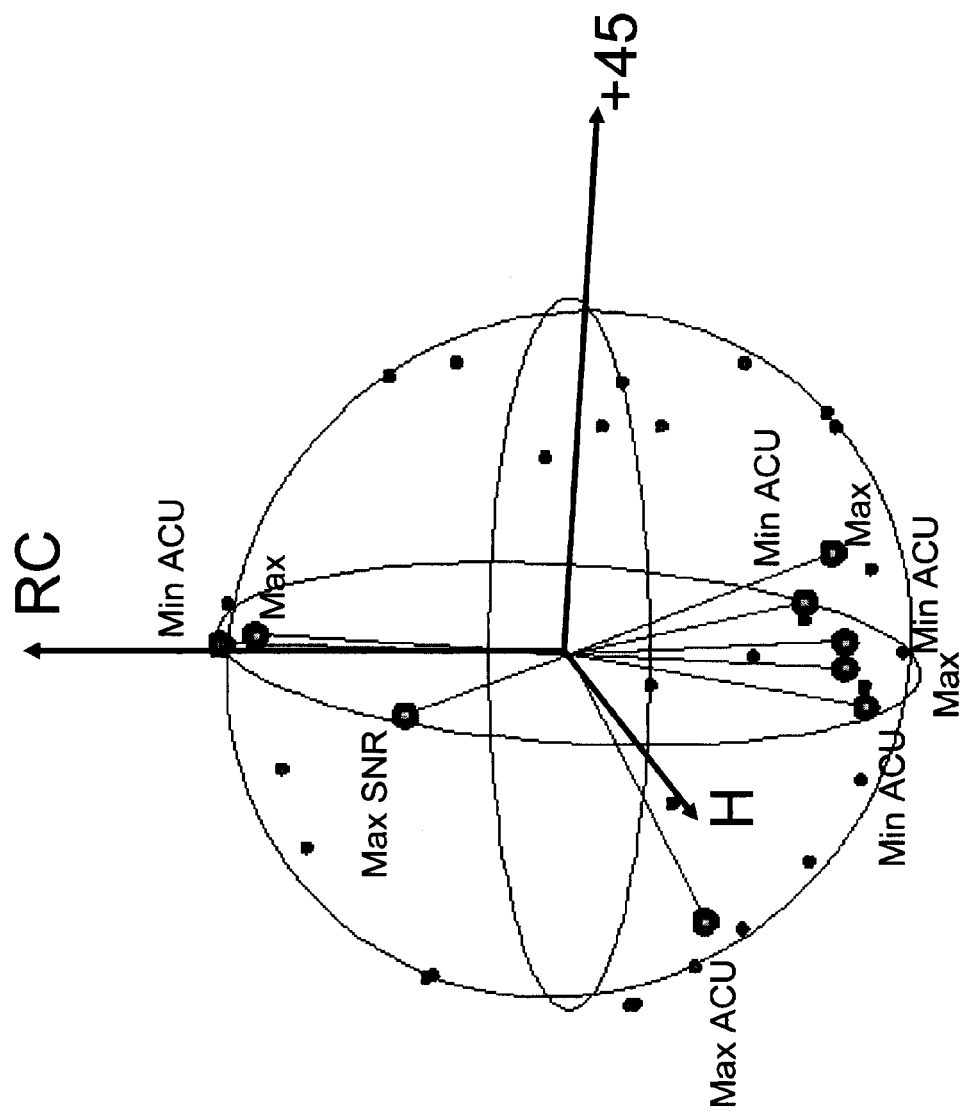

FIG. 6 shows plots of the Stokes vectors for all images evaluated corresponding to the maximum and minimum magnitudes of each of the image quality metrics (SNR, ENT & ACU) on Poincaré spheres. The value on the sphere gives the polarization state that corresponded to images that were evaluated. The vectors with large circles give the polarization states of the images that were preferred for images of specific ONH features. The metrics that were maximized or minimized are labeled. The vectors indicate that images containing circular/elliptical polarization were preferred to linear polarization alone.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims.

REFERENCES

1. J M Bueno & M C W Campbell (2002), *Opt Let* 27:830;
2. S I Guthrie et al. (2004), *Invest Ophthalmol Vis Sci* 45: E-Abstract 2796;
3. S A Burns et al. (2003) *Invest Ophthalmol Vis Sci* 44:4061.
4. A Weber et al. (2004), *Opt Express* 12:5178.

Therefore What is claimed is:
1. An apparatus for imaging the fundus of the eye using non-linearly polarized light, comprising:
a light source for generating a beam of light;
an optical element configured to generate a desired non-linear polarization state of light in said beam of light passing therethrough, wherein said desired non-linear polarization state of light includes any one of circularly polarized light alone and elliptically polarized light alone and excludes linearly polarized light alone;
first light directing and focusing optics configured for directing the beam of light having said desired polarization state onto a fundus of a subject's eye; and
second light directing and focusing optics configured for directing the beam of light reflected from the fundus of a subject's eye into an imaging detector configured for receiving images of the fundus of the eye after illumination by the beam of light, said second light directing and focusing optics being configured for collecting and imaging the beam of light coming from the pupil of the eye with minimal effect on its polarization state.

2. The apparatus according to claim 1 wherein said imaging detector is selected from the group consisting of fundus cameras, scanning laser ophthalmoscopes, confocal scanning laser ophthalmoscopes and optical coherence tomography instruments, with or without wavefront correction.

3. The apparatus according to claim 1 wherein said light source and said optical element are further configured to generate a beam of light having any one of a combination of elliptically polarized light and depolarized light, and a combination of circularly polarized light and depolarized light.

4. The apparatus according to claim 1 including a light depolarizing element located between the optical element and the eye for producing polarization states having a mixture of polarized light and depolarized light in said beam of light.

5. The apparatus according to claim 1 wherein said light source produces linearly polarized light, and wherein said optical element is an optical retarder plate configured to produce any one of said circularly polarized light alone and elliptically polarized light alone.

6. The apparatus according to claim 1 wherein said light source produces linearly polarized light, and wherein said optical element is a quarter wave plate, and including a rotation mechanism connected to said quarter wave plate wherein rotating said quarter wave plate to a first position with respect to an axis of linear polarization of the linearly polarized light entering said quarter wave plate generates elliptically polarized light, and wherein rotating said quarter wave plate to a second position with respect to an axis of linear polarization of the linearly polarized light entering said quarter wave plate for generating circularly polarized light.

7. The apparatus according to claim 1 wherein said first light directing and focusing optics for directing the beam of light onto the fundus of the eye includes an X-Y scanning stage configured to provide displacement of the light beam with respect to the fundus at the rear of the eye.

8. The apparatus according to claim 7 wherein said second light directing and focusing optics includes a confocal pinhole for focusing images of the fundus onto said detector.

9. A method for imaging the fundus of the eye using a beam of non-linearly polarized light, comprising:
   a) generating a beam of non-linearly polarized light having a desired polarization state, the desired polarization state including any one of circularly polarized light alone and elliptically polarized light alone and excluding linearly polarized light alone;
   b) directing and focusing the beam of said non-linearly polarized light onto the fundus of the eye using first light directing and focusing optics; and
   c) directing and focusing a reflected beam of light containing information of the fundus of the eye onto a detector using second light directing and focusing optics, said second light directing and focusing optics being configured for collecting and imaging the beam of light coming from a pupil of the eye with a minimal effect on its polarization state, and producing an image of the fundus of the eye.

10. The method according to claim 9 including analyzing said image of the fundus.

11. The method according to claim 9 wherein said step of generating a beam of non-linearly polarized light includes generating any one of a combination of elliptically polarized light and depolarized light, and a combination of circularly polarized light and depolarized light.

12. The method according to claim 9 wherein said desired polarization state includes any non-linear polarization state generated by combining circularly polarized light with linear polarized light in any direction to produce any type of elliptically polarized light.

13. The method according to claim 9 wherein said step of generating a beam of non-linearly polarized light includes producing two perpendicular polarizations of light with differing relative intensities incident on a retarder which causes the two polarizations to be out of phase by an amount different from 0 degrees thereby producing elliptically polarized light.

14. The method according to claim 13 wherein said two polarizations are out of phase by an amount of 90 or 180 degrees.

15. The method according to claim 9 wherein said step of generating a beam of non-linearly polarized light includes producing two oppositely rotating circular polarizations of light with differing relative intensities and combining the two oppositely rotating circular polarizations of light thereby producing elliptically polarized light.

16. The method according to claim 10 including repeating steps a), b) and c) for four different states of polarization of the beam of non-linearly polarized light including circularly and elliptically polarized states of light, and wherein said step of analyzing said image of the fundus includes producing images corresponding to the light beam with circularly and elliptically polarized states other than those states used to record original images.

17. The method according to claim 9 wherein said step of generating a beam of non-linearly polarized light includes generating elliptically or circularly polarized light in combination with depolarized light.

* * * * *